United States Patent [19]
Viera

[11] Patent Number: 5,322,508
[45] Date of Patent: Jun. 21, 1994

[54] GUIDEWIRE FLUID DELIVERY SYSTEM AND METHOD OF USE

[75] Inventor: Fernando M. Viera, Hialeah, Fla.

[73] Assignee: Cordis Corporation, Miami Lakes, Fla.

[21] Appl. No.: 44,966

[22] Filed: Apr. 8, 1993

[51] Int. Cl.$^5$ .............................................. A61M 31/00
[52] U.S. Cl. ..................................................... 604/52
[58] Field of Search .................. 128/656–658, 128/772; 604/30, 35, 93, 95, 96, 280, 52, 49

[56] References Cited

U.S. PATENT DOCUMENTS

| | | | |
|---|---|---|---|
| 623,022 | 4/1899 | Johnson | 604/280 |
| 4,538,622 | 9/1985 | Samson et al. | 128/772 |
| 4,619,274 | 10/1986 | Morrison | 128/772 |
| 4,715,378 | 12/1987 | Pope et al. | 604/194 |
| 4,721,117 | 1/1988 | Mar et al. | 128/772 |
| 4,827,941 | 5/1989 | Taylor et al. | 128/657 |
| 4,846,186 | 7/1989 | Box et al. | 128/657 |
| 4,846,193 | 7/1989 | Tremulis et al. | 128/772 |
| 4,984,581 | 1/1991 | Stice | 128/772 |

*Primary Examiner*—Jerome L. Kruter
*Attorney, Agent, or Firm*—Lockwood, Alex, Fitzgibbon & Cummings

[57] ABSTRACT

A guidewire fluid delivery system is provided which is both a steerable guidewire and a mechanism for the delivery or withdrawal of fluid between a location outside of the body and a location distally within the body. A passageway is provided which directs fluid flow generally along the elongated coil of the guidewire. A treatment procedure is also provided whereby fluids are delivered to a distal location and/or withdrawn from a distal location during a procedure, the primary component of which is insertion of a fluid-delivery guidewire device.

25 Claims, 1 Drawing Sheet

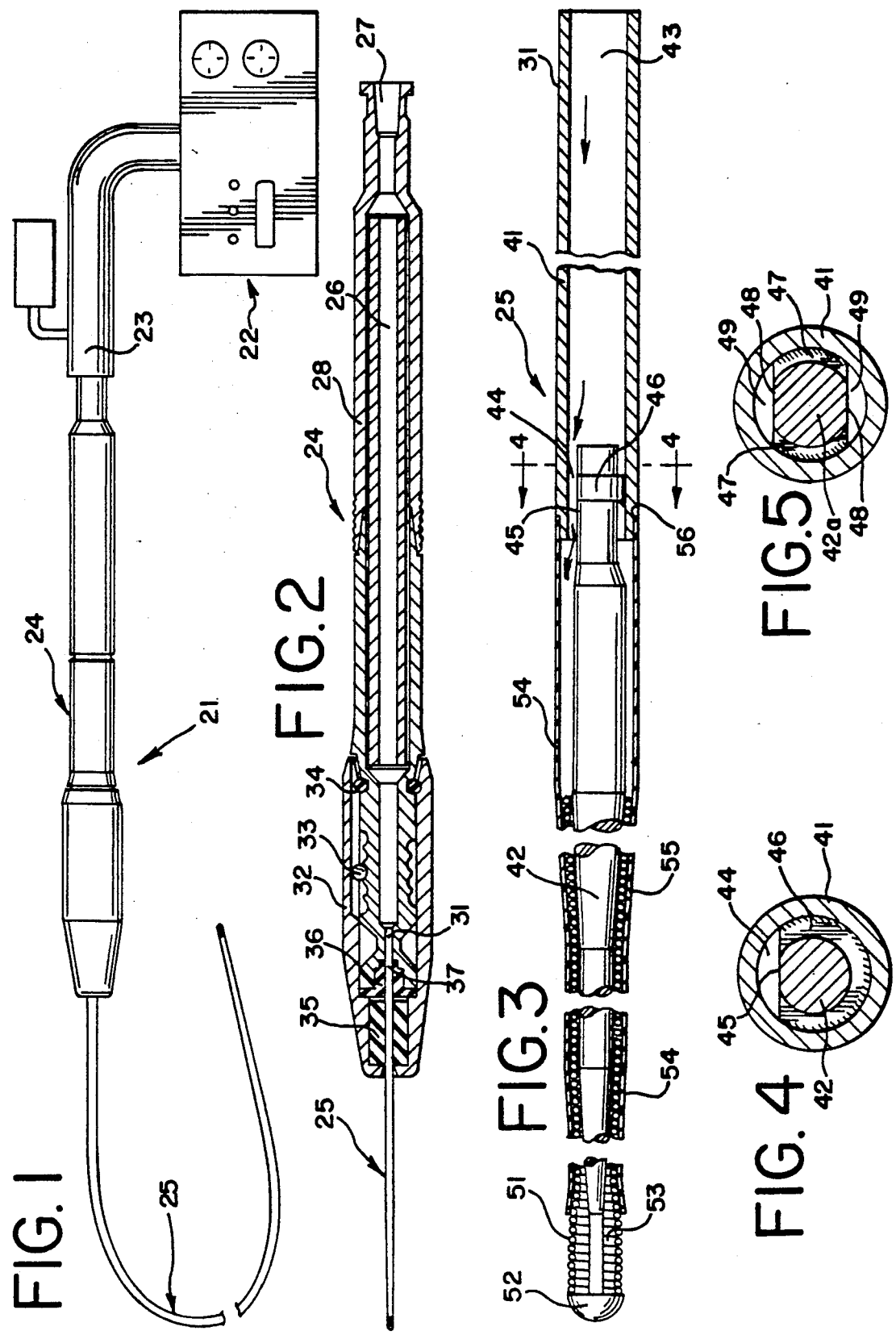

GUIDEWIRE FLUID DELIVERY SYSTEM AND METHOD OF USE

BACKGROUND AND DESCRIPTION OF THE INVENTION

The present invention generally relates to medical devices for the delivery of fluids transluminally. The fluid delivery system takes the general form of an elongated medical device guidewire and thus enjoys the advantageous features of a guidewire, especially its maneuverability and relatively small external diameter when compared with catheter systems typically utilized for fluid delivery procedures. The guidewire fluid delivery system of this invention includes a through lumen that is in fluid-passing communication with a passageway which is generally co-extensive with an elongated coil component of the guidewire system. Fluid passing through the through lumen exits the guidewire fluid delivery system at any number of selected delivery locations, typically along the coil, which can include at the distal tip of the guidewire.

During the course of various medical treatments and procedures, it is essential or desirable to deliver fluids to specific locations within the body. Such procedures are, in general, well-known, and a variety of catheter devices are available for achieving fluid delivery in this regard. Typically, devices to accomplish these types of fluid delivery procedures require a system that combines a steerable guidewire and a separate fluid-delivery catheter which is guided in place by the steerable guidewire.

More specifically, a typical fluid delivery procedure incorporates the use of a generally solid guidewire in combination with the use of a fluid-delivery catheter. A guidewire is a device having excellent steerability and has a particularly narrow diameter, thereby facilitating its insertion into body passageways. Guidewires are generally designed to be maneuverable through narrow, tortuous and/or branching body passageways. Once inserted to the desired location, a guidewire provides the track over which a catheter then passes until the catheter is positioned along a pathway which is virtually the same as that of the inserted guidewire. In essence, the lumen of the catheter is threaded over the guidewire. Typically, the catheter lumen also serves as the passageway for delivery of fluids to the desired location within the body. Accordingly, before fluid delivery can actually occur, it is necessary to carefully remove the guidewire from the body and hence from out of the lumen of the fluid-delivery catheter.

This type of fluid delivery system accordingly requires three basic steps: insertion or implantation of the steerable guidewire, passage of the fluid-delivery catheter over the inserted guidewire, and removal of the guidewire from out of the lumen of the thus implanted or inserted catheter. The catheter is then ready for fluid delivery therethrough. Each of these steps must be done carefully and requires a noticeable amount of time, even for the most skilled surgeon. In addition, because the fluid-delivery catheter must fit over the steerable guidewire, the profile of the combination delivery system is significantly larger than the external diameter or profile of the steerable guidewire itself. Because of this, these types of combination systems are limited in their applications. They are generally not suitable for very narrow passageways, such as especially remote vessel locations and locations within the brain.

Accordingly, there is a need for a medical device fluid delivery system which has an especially thin profile or diameter to enable it to safely pass to and/or through very narrow and/or particularly delicate locations. It would also be advantageous to avoid a multiple-step insertion procedure in favor of a procedure whereby fluid delivery is accomplished directly by a device having the properties of a steerable guidewire. In other instances, it is advantageous that such a fluid-delivery steerable guidewire be used in association with a catheter positioned thereover in an arrangement in which the catheter performs a specific function, such as an angioplasty procedure, while the steerable guidewire remains in place and delivers needed fluids, such as blood or blood components, to a location distal of the lesion or the like being treated during an angioplasty procedure or the like. It would also be useful if such a steerable guidewire system could be provided which has the ability to distally remove fluids from a location within the body.

In summary, the present invention achieves these objectives and provides advantageous results along these lines by providing a guidewire having the capability to pass fluid therethrough. The elongated medical device guidewire having fluid delivery and removal capabilities combines an elongated corewire surrounded at least in part by an elongated coil. A tubing member or sleeve generally covers the elongated coil and is made of a material which prevents passage of fluid, particularly liquids, therethrough, except at a designated location or at designated locations which can include an area of the coil that is distal of the distal edge of the tubing member. Through the use of an appropriate handle assembly, a fluid can be delivered into the fluid-delivery guidewire whereby the fluid flows between the elongated corewire and the tubing member or sleeve and generally along the elongated coil until reaching the delivery location or locations at which the fluid passes out of the fluid-delivery guidewire.

It is a general object of the present invention to provide an improved guidewire fluid delivery system and procedure for using the system.

Another object of the present invention is to provide an improved guidewire fluid delivery system through which fluids can be transferred without the need for a catheter positioned thereover.

Another object of this invention is to provide an improved medical device guidewire which includes means for the passage of fluids through the guidewire device while utilizing a solid corewire.

Another object of the present invention is to provide a guidewire fluid delivery system wherein fluids generally follow the elongated coil of the guidewire device.

Another object of the present invention is to provide an improved procedure for treating internal body conditions by fluid delivery or removal through a guidewire itself and without requiring either a catheter to be passed thereover or removal of the guidewire before fluid flow can be initiated.

These and other objects, features and advantages of this invention will be clearly understood through a consideration of the following detailed description.

BRIEF DESCRIPTION OF THE DRAWINGS

The invention will be further elucidated in the following description with reference to the accompanying drawings in which:

FIG. 1 is a generally schematic elevational view of the guidewire fluid delivery system in use with an inflation device.

FIG. 2 is a longitudinal cross-sectional view through the preferred guidewire fluid delivery system having a handle assembly suitable for use in conjunction therewith.

FIG. 3 is an enlarged longitudinal view, partially in cross-section, of the preferred fluid delivery guidewire.

FIG. 4 is a cross-sectional view along the line 4—4 of FIG. 3.

FIG. 5 is a cross-sectional view similar to FIG. 4 and illustrating an embodiment variation.

DESCRIPTION OF THE PARTICULAR EMBODIMENTS

A guidewire fluid delivery system, generally designated at 21, is illustrated in FIG. 1. Also included is a somewhat schematic representation of a typical piece of equipment for delivering fluids through catheters and the like, such equipment being generally known as an inflation device, this equipment being generally designated as 22. An inflation device has known mechanisms, typically including a syringe arrangement by which fluids are moved either distally or proximally, that is either into or out of the body, when a suitable fluid passage device such as a catheter is affixed to the outlet end 23 of the inflation device, typically by means of a suitable luer connection assembly or the like. Inflation device contains means for passing precise quantities of fluids, typically liquids, therethrough and thus through the catheter or the like secured thereto at the outlet end 23.

The illustrated guidewire system 21 includes a handle assembly, generally designated 24, and a fluid-passing guidewire assembly, generally designated 25. Referring to FIG. 2, handle assembly 24 can be of any suitable type, provided it includes an arrangement for fluid passage. Illustrated handle assembly 24 is of a generally known construction and includes a through lumen 26 allowing passage of fluids through the handle assembly 24.

The illustrated handle assembly 24 further includes a luer connector 27 of generally known construction and which mates with a connector of the inflation device 22 or the like. The through lumen 26 passes through handle body 28, which receives and supports proximal end portion 31 of the fluid-passing guidewire assembly 25. An ergonomic mechanism 32 is used to control steering of the device. An anti-friction member 33 facilitates rotational movement of the handle body 28 and thus of the fluid-passing guidewire assembly 25 with respect to the ergonomic mechanism 32, which can facilitate maneuvering of the guidewire assembly 25 within the body. Appropriate seals are also provided, such as an 0-ring 34, a block seal 35, and intermediate seal 36, any or all of which can be made out of suitable materials such as silicone, artificial rubbers, and other materials approved for use in medical devices. It will be appreciated that the handle assembly 24 at all times remains outside of the body, while the fluid-passing guidewire assembly 25 enters the body during use and can, depending upon the procedure and the relative sizes of the guidewire and of the patient, move substantially completely into the body.

The preferred fluid-passing guidewire assembly 25 is illustrated in greater detail in FIG. 3. A hypotube 41 is at the proximal end portion 31 of the guidewire assembly. The hypotube 41 is essentially a hollow polymeric or metallic tube which is sized to fit within passageway 37 of the handle assembly 24 or other suitable handle component of the system. The handle assembly and its seals are designed to minimize any undesired fluid passage at this slidable connection between the handle assembly and the fluid-passing guidewire assembly 25.

A corewire 42 is secured to the hypotube 41 in a manner by which fluid can pass between the corewire and the hypotube. More particularly, fluid passes between lumen 43 of the hypotube 41 and the external surface of the solid corewire 42. Typically, corewire 42 is made of metal or other material exhibiting the requisite degree of torsional rigidity normally associated with medical device guidewires. In the embodiment illustrated in FIGS. 3 and 4, this passageway includes an open area 44 defined by a flat 45 along a proximal end portion of the corewire 42. Securement of the proximal end portion of the corewire 42 to the distal end portion of the hypotube 41 can be carried out by any suitable means such as the illustrated flap or bracket 46 affixed to both the corewire 42 and the hypotube 41 by suitable means, such as welding, adhesives, casting, molding or the like.

Exemplary of other embodiments which can be used to secure the hypotube 41 and the corewire together while permitting fluid passage through the connection area is the embodiment illustrated in FIG. 5. Here, the attachment is provided by bracket or brackets 47. A plurality of flats 48 (two being shown) are provided on the proximal end of a corewire 42a, and a plurality of open areas 49 are thus presented.

With further reference to FIG. 3, an elongated coil 51 surrounds a substantial portion of the corewire 42. Typically, the elongated coil 51 is secured, such as by welding, adhesives or other suitable treatment or means, to the corewire at least at the proximal end and distal end of the coil 51. In a somewhat customary manner, it is preferred that this bonding at the distal end takes the form of or includes a rounded or hemispherical configuration in order to provide an especially atraumatic tip 52 for the fluid-passing guidewire assembly 25. Often it is advantageous that the elongated coil 51 be manufactured so as to exhibit either radio-opaque or radiolucent properties. It will be noted that the coil 51 can closely overlie and engage the corewire 42 throughout much of its length. At the distal end portion in the preferred embodiment, as illustrated, the inner surface defined by the coil 51 is spaced from the external surface of the corewire 42, thereby providing a fluid passageway pocket 53 therebetween which can facilitate distribution of fluids in accordance with the present invention at this distal portion location.

An external sleeve 54 further defines the fluid passageway characteristic of the guidewire assembly 25. Sleeve 54 is preferably constructed of a tough polymeric material such as polytetrafluoroethylene (Teflon), or the like. In the illustrated embodiment, this external sleeve 54 extends from the hypotube 41 to the distal end portion of the corewire 42 and coil 51 such that a distal end portion of the elongated coil 51 is unsleeved. If desired, this distal end portion could be partially sleeved, although it has been found that the fully unsleeved or fully uncovered distal end portion as illustrated in FIG. 3 provides a fluid flow path which does not present excessive resistance to fluid flow which is developed by the operation of a typical inflation device 22. It will be appreciated, that, with an arrangement as illustrated in FIG. 3, the fluid passes between turns of the coil 51 at the distal end portion of the guidewire assembly 25.

It is also possible to include one or more perforations 55 through the sleeve 54 at a desired location or locations therealong. In this way, fluid flowing between the corewire 42 and the external sleeve 54 will pass through the elongated coil 51 at a location or locations other than and proximal to the distal end portion fluid passageway 53 pocket. This permits a structure having one or more fluid transfer locations between the corewire 42 and the external surface of the guidewire assembly 25 at which fluid is delivered or received. It will be appreciated that the external sleeve 54 will, to the extent that it is present and unperforated, prevent fluid from escaping the coiled section and as a result direct the fluid to the unsleeved locations, such as at the distal end portion fluid passageway pocket 53 and at any perforations 55. Accordingly, fluid flow can be at just the distal tip portion and not anywhere along the sleeve, at perforations along the sleeve and not at the distal tip portion, or at both the distal tip portion and at one or more perforations along the sleeve.

The guidewire fluid delivery system in accordance with the invention can be used, for example, to deliver contrast media or other media, to administer localized drug therapy, or to remove fluid, such as from brain passageways, knees, or other locations where undesirable fluid buildup can be experienced. Exemplary applications include those which be characterized as coronary, peripheral and neurological. While not specifically illustrated, this device can be fashioned as an extendable guidewire in order to provide an even more versatile system.

A typical guidewire fluid delivery system in accordance with this invention can be structured to have an outer diameter of the guidewire assembly 25 which is as small as about 0.014 inch, even as small as about 0.012 inch. The diameter should be large enough so that fluid can pass through in a reasonably rapid fashion and in a manner which avoids an overly restrictive flow pathway. For example, a hypotube having an outer diameter of 0.014 inch typically possesses an internal diameter of 0.0105 inch. An exemplary corewire will be between about 30 and about 32 inches long. An exemplary external sleeve having the structure and properties illustrated in FIG. 3 will be approximately 28 inches long. Preferably, there is an overlap of about 1 inch between the external sleeve and the hypotube, with the hypotube preferably having a recessed area or step 56 to provide a smooth outer surface for the device.

A system of the type illustrated herein and having an outer diameter of the fluid-passing guidewire assembly 25 of 0.014 inch was attached to a conventional inflation device 22, which was then activated. During this bench test, the inflation device registered at 1½ atmosphere, which generally corresponds to about 20 psi. The fluid used was contrast media, which readily flowed through the device, exiting therefrom between the coil turns and the distal end portion of the device.

The procedure of the present invention is of enhanced simplicity when compared with other procedures for achieving the objective of delivering fluids into or out of the body. The guidewire fluid delivery system operates as both a steerable guidewire and a fluid delivery system during a single insertion into the body. There is no need to insert a catheter over a steerable guidewire. Nor is there a need to remove the steerable guidewire before being able to pass the fluid through the device and to or from the desired distal location within the body. Instead, the guidewire fluid delivery system is used to position the fluid-passing guidewire assembly to the proper location by customary steering and positioning procedures. Immediately upon being positioned to the proper location, the desired fluid can be passed therethrough, such as through the use of a known inflation device or device which will generate vacuum conditions. For example, contrast media can be immediately delivered as soon as the fluid-passing guidewire assembly is inserted in place.

In a related procedure, the guidewire fluid delivery system can be utilized as a steerable guidewire for properly positioning a balloon catheter, such as for an angioplasty procedure, at a lesion or other treatment location. Upon balloon inflation or other similar procedure, blood flow across the lesion or the like typically is all but stopped by the device during actual treatment. By this procedure in accordance with the present invention, the guidewire fluid delivery system can be used to deliver blood, blood components or other desirable fluid through the distal end portion of the guidewire, thereby, in effect, providing flow of blood or the like to locations distal of the lesion or the like which is being treated.

It will be understood that the embodiments of the present invention which have been described are illustrative of some of the applications of the principles of the present invention. Numerous modifications may be made by those skilled in the art without departing from the true spirit and scope of the invention.

I claim:

1. An elongated medical device guidewire fluid delivery system having a proximal end and a distal end, the guidewire system comprising:

an elongated corewire having a proximal end portion, a distal tip portion and an elongated external surface;

an elongated coil surrounding at least a portion of the elongated external surface of the elongated corewire, said elongated coil extending to the distal tip portion of the elongated corewise, said elongated coil having an external surface, an internal surface and a plurality of generally adjacent coil windings;

a handle assembly at the proximal end of the guidewire system, the handle assembly having a through lumen;

a hypotube defining a passageway generally coextensive with said through lumen of the handle assembly, said hypotube having a lumen and being secured to said elongated corewire, said hypotube and said passageway extending from said through lumen to the proximal end portion of the elongated corewire, said passageway providing fluid-passing communication from the proximal end portion of said corewire and along said elongated external surface of the corewire;

said passageway distal of the through lumen of the handle assembly includes an open area between at least a distal portion of said hypotube and at least the proximal end portion of the elongated corewire;

a sleeve member covering a substantial portion of the external surface of said elongated coil; and at least one fluid transfer location at which said elongated coil is uncovered by said sleeve member, whereby fluid passing through said passageway exits or enters said guidewire system at said fluid transfer location.

2. The guidewire fluid delivery system in accordance with claim 1, wherein said fluid transfer location is at an unsleeved distal end portion of said elongated coil, said fluid transfer location being along said distal tip portion of the elongated corewire and said distal tip portion of the elongated coil.

3. The guidewire fluid delivery system in accordance with claim 2, wherein said external surface of the elongated corewire at the distal end portion thereof is spaced from said internal surface of the coil windings at the distal end portion thereof, thereby defining a distal end portion fluid passageway pocket therebetween.

4. The guidewire fluid delivery system in accordance with claim 1, wherein said sleeve member includes a perforation along its length in order to define said fluid transfer location.

5. The guidewire fluid delivery system in accordance with claim 1, wherein said elongated coil extends distally beyond a distal edge of the sleeve member in order to define one said fluid transfer location, and wherein said sleeve member includes at least one perforation along its length in order to define another said fluid transfer location.

6. The guidewire fluid delivery system in accordance with claim 1, wherein said hypotube is secured at its said distal portion to the proximal end portion of the elongated corewire, and said hypotube is substantially coaxial with the through lumen of the handle assembly.

7. The guidewire fluid delivery system in accordance with claim 1, wherein said elongated corewise has a flattened portion at its proximal end portion to at least partially define said open area between said flattened portion and the lumen of said hypotube.

8. The guidewire fluid delivery system in accordance with claim 7, wherein said elongated corewire has at least two said flattened sections at its proximal end portion.

9. The guidewire fluid delivery system in accordance with claim 1, wherein the sleeve member is secured to the hypotube in order to further define said passageway.

10. The guidewire fluid delivery system in accordance with claim 1, wherein said corewire is solid and devoid at any axial passageway therethrough.

11. The guidewire fluid delivery system in accordance with claim 1, wherein said elongated external surface of the corewire engages said internal surface of the coil along substantially the entire length of the coil.

12. An elongated medical device fluid-passing guidewise assembly having a proximal end and a distal end, the fluid-passing guidewire assembly comprising:

an elongated corewise having a proximal end portion, a distal tip portion and an elongated external surface;

an elongated coil surrounding at least a portion of the elongated external surface of the elongated corewire, said elongated coil extending to the distal tip portion of the elongated corewise, the elongated coil having an external surface, an internal surface, and a plurality of generally adjacent coil windings;

a sleeve covering a substantial portion of the external surface of said elongated coil;

a fluid-passing passageway defined between the external surface of said elongated corewise and said sleeve, said elongated coil being positioned along at least a portion of said fluid-passing passageway;

a hypotube further defining at least a portion of said fluid-passing passageway proximal of said coil, said passageway including an open area between at least a distal portion of said hypotube and at least the proximal end portion of the elongated corewire; and at least one fluid transfer location at which said elongated coil is unsleeved by said sleeve, whereby fluid passing through said passageway exits or enters said fluid-delivery guidewise assembly at said fluid transfer location.

13. The fluid-passing guidewire assembly in accordance with claim 12, wherein said fluid transfer location is along said distal tip portion of the elongated corewire and said distal tip portion of the elongated coil.

14. The fluid-passing guidewire in accordance with claim 12, wherein said external surface of the elongated corewise at the distal end portion thereof is spaced from said internal surface of the coil windings at the distal end portion thereof, thereby defining a distal end portion fluid passageway pocket therebetween.

15. The fluid-passing guidewire in accordance with claim 12, wherein said sleeve member includes a perforation along its length in order to define said fluid transfer location.

16. The fluid-passing guidewire in accordance with claim 12, wherein said elongated coil extends distally beyond a distal edge of the sleeve member in order to define one said fluid transfer location, and wherein said sleeve member includes at least one perforation along its length in order to define another said fluid transfer location.

17. The fluid-passing guidewire in accordance with claim 12, wherein said hypotube is secured at its distal end portion to the proximal end portion of the elongated corewire.

18. The fluid-passing guidewire in accordance with claim 12, wherein said elongated corewise has a flattened portion at its proximal end portion to at least partially define said open area between said flattened portion and the lumen of said hypotube.

19. A procedure for passing liquids between a distal location within a body passageway and a location outside of the body without requiring removal of the guidewire from the body, the procedure comprising the steps of:

providing an elongated medical device guidewise fluid delivery assembly having a liquid-passing passageway between an elongated corewise thereof and an external sleeve thereof, the passageway including a section generally along an elongated coil disposed between the elongated corewise and the sleeve;

introducing the guidewise fluid delivery assembly into a body, through a body passageway thereof, and to a distal location within the body passageway at which liquid is to be delivered or withdrawn;

connecting a proximal end of the guidewise liquid delivery assembly with a liquid movement means for initiating and effecting passage of liquid through an elongated device permitting passage of liquid therethrough; and activating the liquid movement means in order to move liquid through the guidewise liquid delivery assembly between the distal location within the body passageway and the proximal end of the guidewise liquid delivery assembly.

20. The procedure in accordance with claim 19, wherein said introducing step includes maneuvering the guidewire liquid delivery assembly through tortuous and narrow passageways within the body, said maneuvering step being carried out from a location outside of the body.

21. The procedure in accordance with claim 19, wherein said procedure delivers media from the liquid movement means to the distal location within the body passageway.

22. The procedure in accordance with claim 19, wherein said procedure withdraws liquid from the distal location within the body passageway to outside the body.

23. The procedure in accordance with claim 19, further including inserting a dilatation within the body and along the guidewire liquid delivery assembly, effecting a dilatation procedure which generally blocks the body passageway thereat while generally simultaneously flowing liquid through the guidewire liquid delivery assembly and to a location distal of the location of the dilatation procedure.

24. A procedure for passing fluids between a distal location within a body passageway and a location outside of the body without requiring removal of the guidewire from the body, the procedure comprising the steps of:

providing an elongated medical device guidewire fluid delivery assembly having a fluid-passing passageway between an elongated corewire thereof and an external sleeve thereof, the passageway including a section generally along an elongated coil disposed between the elongated corewire and the sleeve;

introducing the guidewire fluid delivery assembly into a body, through a body passageway thereof, and to a distal location within the body passageway at which fluid is to be delivered or withdrawn;

connecting a proximal end of the guidewire fluid delivery assembly with a fluid movement means for initiating and effecting passage of fluid through an elongated device permitting passage of fluid therethrough;

activating the fluid movement means in order to move fluid through the guidewire fluid delivery assembly between the distal location within the body passageway and the proximal end of the guidewire fluid delivery assembly; and inserting a dilatation catheter within the body and along the guidewire fluid delivery assembly, effecting a dilatation procedure which generally blocks the body passageway thereat while generally simultaneously flowing blood or a blood component through the guidewire fluid delivery assembly and to a location distal of the location of the dilatation procedure.

25. The procedure in accordance with claim 24, wherein said procedure is an angioplasty procedure.

* * * * *